United States Patent [19]

Blosser et al.

[11] Patent Number: 5,730,294
[45] Date of Patent: Mar. 24, 1998

[54] DESIGNER TAMPON CASE

[76] Inventors: Jean Blosser, 1189 Scenic Crest, Uniontown, Ohio 44685; Julie Atwood, 100 Main St. #5, Boston, Mass. 02129

[21] Appl. No.: 647,360

[22] Filed: May 9, 1996

[51] Int. Cl.$^6$ ........................................ B65D 25/04
[52] U.S. Cl. ..................... 206/581; 206/440; 206/823
[58] Field of Search ........................... 206/581, 823, 206/812, 438, 440, 494, 457, 38

[56] References Cited

U.S. PATENT DOCUMENTS 5,261,531  11/1993  Nieves ............................ 206/440 X
5,579,916  12/1996  Manko ............................ 206/440 X Primary Examiner—Jacob K. Ackun
Attorney, Agent, or Firm—Roger D. Emerson

[57] ABSTRACT

An article for protectively and discreetly transporting feminine hygiene products, particularly tampons, is provided. The article includes a crush-resistant, moisture-resistant housing. Disposed within the housing is a support member having a plurality of concave channels therein for the reception of tampons and their associated applicators. The support member holds the tampons in a fixed relationship while supporting them from being crushed during transport. The housing includes a decorative exterior layer to minimize embarrassment if the article is viewed in public. The article further comprises a releasably secured cover which may include interior or exterior pockets for the transport of additional items.

17 Claims, 5 Drawing Sheets

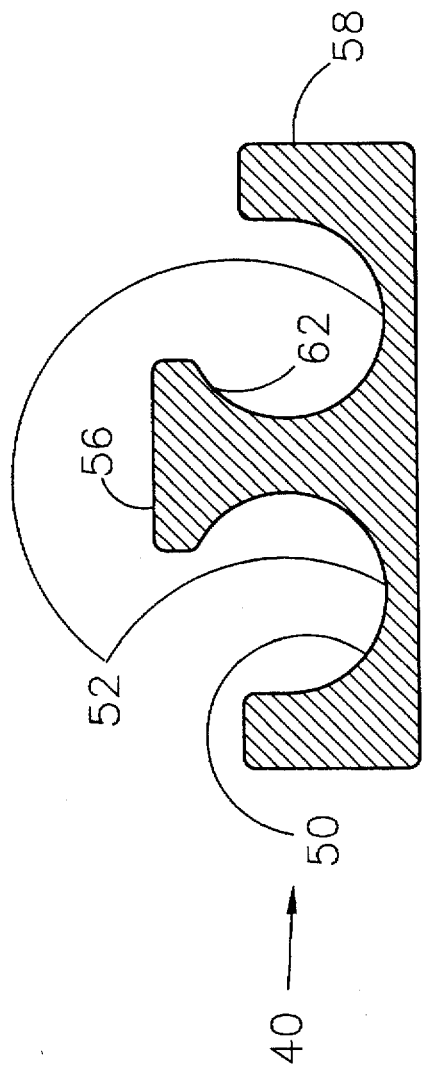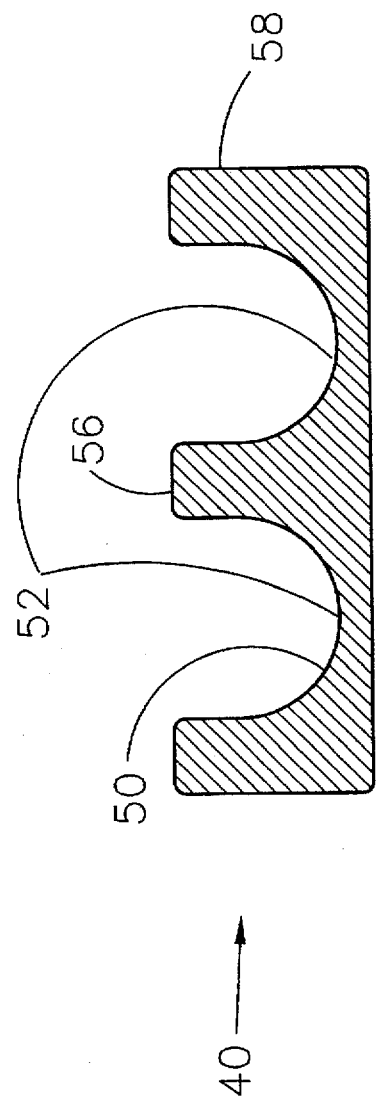

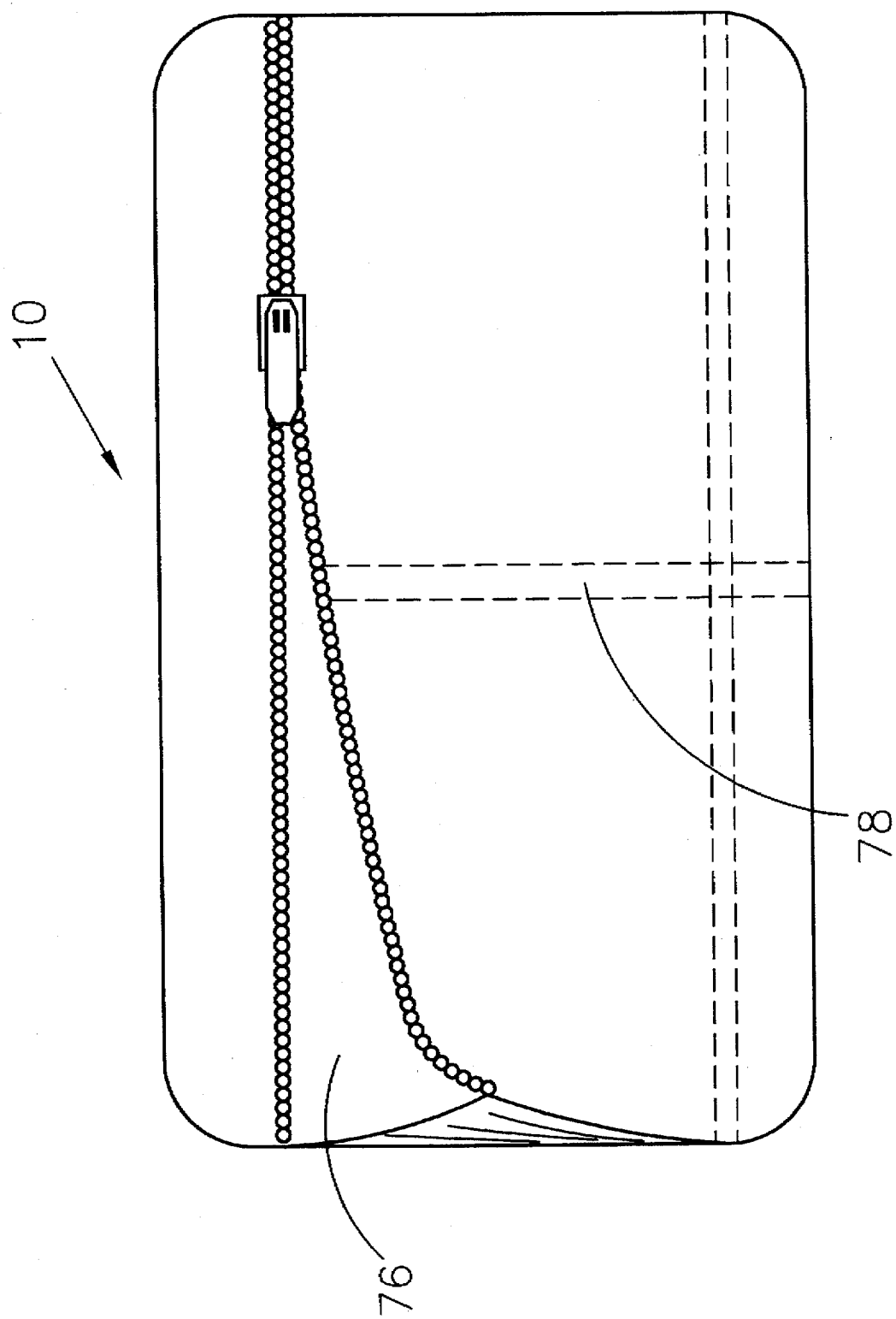

DESIGNER TAMPON CASE

BACKGROUND OF THE INVENTION

1. Field of Invention

This invention pertains to articles for carrying personal items, and more specifically to articles for discretely carrying feminine hygiene products.

2. Description of the Related Art

It is recognized that convenient access to feminine hygiene products is a necessity for many women. To that end, many women carry tampons, sanitary pads, panty shields, and the like in their purses, briefcases, or pockets. Unfortunately, women often find that the unprotected tampons become crushed and unusable when they are so carried. In addition, the paper or plastic covering for the feminine hygiene products may tear, making the items susceptible to moisture or contamination, rendering them useless or unsanitary. Finally, many women find it embarrassing when feminine hygiene products they are carrying are viewed in public, such as when a purse is opened.

There have been methods and apparatuses presented in the art to provide discrete means of carrying such items. For example, a wallet-like carrying case having a pocket therein for the insertion of a tampon or sanitary napkin is disclosed in U.S. Pat. No. 4,286,639 to Murphy. The carrying case is essentially flat and does not provide crush resistance for a tampon held therein.

Another wallet-like assembly is disclosed in U.S. Pat. No. 5,046,620 to Barabino. The multi-compartmental assembly includes a supple partition to separate feminine hygiene products from more frequently accessed items such as cosmetics. Again, a tampon held within the partitioned storage area is susceptible to being crushed.

Another container the applicant is aware of is essentially a two-piece plastic tube with closed ends. Tampons can be carried in the tube in a water-resistant, crush-resistant container. However, the embarrassment factor is not alleviated because the container has the size and shape of a tampon. In addition, such a container makes no provision for other necessary items such as panty shields, coins, or pills.

Another container the applicant is aware of has a plastic base with a flip-open lid. The base is adapted to carry one or more tampons therein. In addition, the container provides a separate compartment for carrying pills which is accessed through a second flip-open lid. This container does not support tampons carried therein in a predetermined position thereby making them susceptible to damage. The plastic container is also susceptible to damage.

The present invention provides new and improved means for discretely carrying personal items in a way which simply and effectively overcomes the problems currently encountered in the art.

SUMMARY OF THE INVENTION

In accordance with the practice of the present invention, there is provided an article for discretely carrying feminine hygiene products which protects the items carried therein.

More particularly, in accordance with the present invention, an article for protectively and discretely transporting at least two tampons is provided.

In accordance with one aspect of the invention, the article comprises a housing, including a bottom, a front wall, a rear wall, and opposite side walls, and an open top disposed in communication with an interior of the housing. The housing includes a first exterior layer and a second interior layer, the exterior layer being made of a first material and the interior layer being made of a second, moisture-resistant material. The article also comprises a cover attached along one edge thereof to the back wall of the housing and disposed for placement in a covering relationship to the interior of the housing. A support member disposed within the housing has a first surface with a plurality of parallel concave channels therein, adjacent channels being separated an by upwardly extending partition. The article further includes means for releasably securing the cover in the covering relationship.

In accordance with another aspect of the invention, the housing further comprises stiffening means for stiffening the housing, the stiffening means being disposed between said exterior layer and said interior layer.

In accordance with another aspect of the invention, the support member engages a portion of the cover when the cover is placed in the covering relationship.

In accordance with another aspect of the invention, the partition includes oppositely extending flanges.

In accordance with another aspect of the invention, the cover comprises an interior surface having a pocket therein.

In accordance with another aspect of the invention, the cover comprises an exterior surface having a pocket therein.

One advantage of the present invention is that more than one tampon can be protectively and discretely carried by a woman needing convenient access to the items.

Another advantage of the present invention is the crush-resistant housing which retains the original shape of a tampon carried therein.

Another advantage of the present invention is the moisture-resistant lining which protects the feminine hygiene products from unsanitary conditions.

Another advantage of the present invention is the appearance of the article which minimizes public embarrassment.

Still other benefits and advantages of the invention will become apparent to those skilled in the art to which it pertains upon a reading and understanding of the following detailed specification.

BRIEF DESCRIPTION OF THE DRAWINGS

The invention may take physical form in certain parts and arrangement of parts, a preferred embodiment of which will be described in detail in this specification and illustrated in the accompanying drawings which form a part hereof and wherein:

FIG. 4 is a transverse sectional view of one embodiment of a support member according to the present invention.

FIG. 5 is a transverse sectional view of a further embodiment of the support member according to the invention.

FIG. 7 is a top view of the article of the present invention having the cover in a covering relationship.

DESCRIPTION OF THE PREFERRED EMBODIMENT

Figure 1:
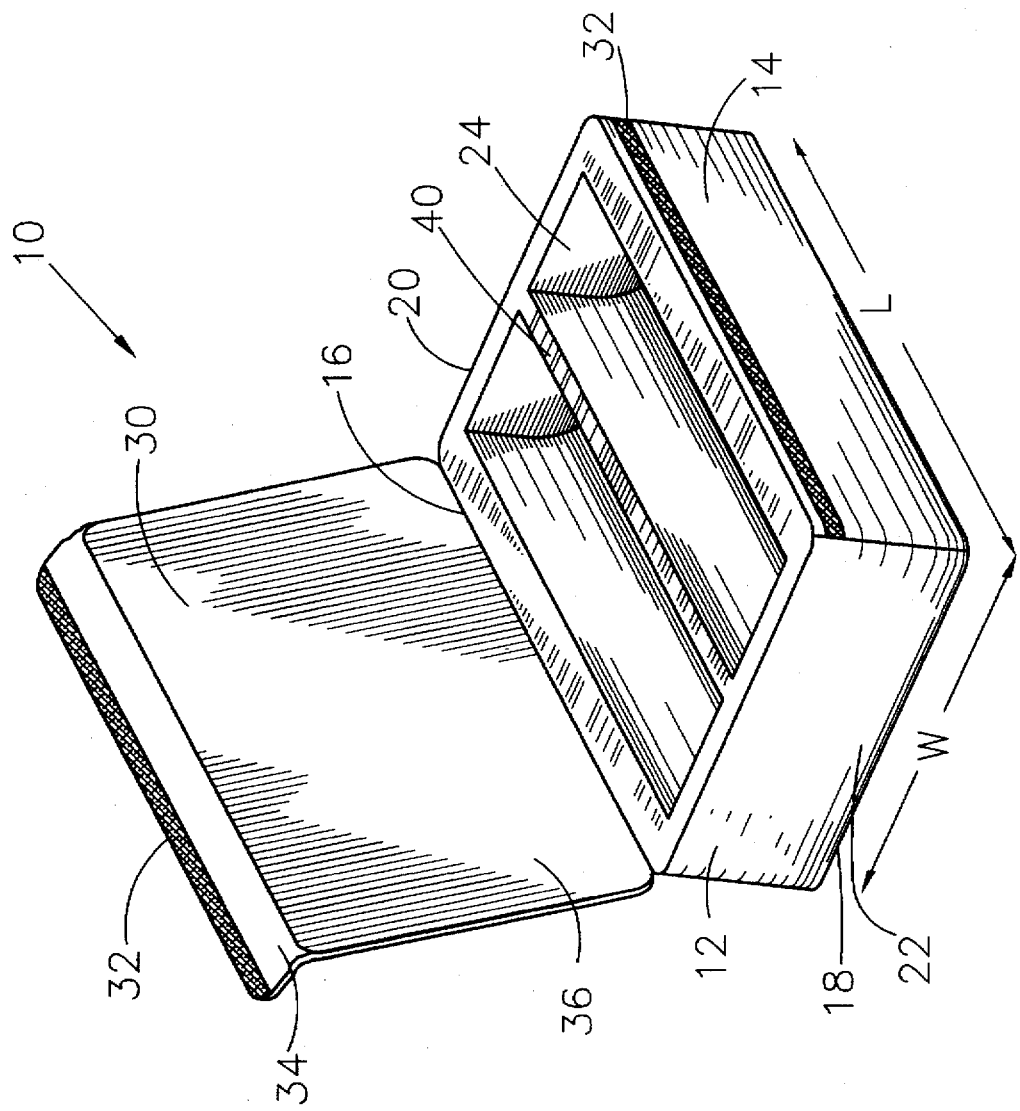
FIG. 1 is a perspective view of an article for transporting feminine hygiene products according to the invention.

Referring now to the drawings wherein the showings are for purposes of illustrating a preferred embodiment of the invention only and not for purposes of limiting the same, FIG. 1 shows an article 10 for transporting feminine hygiene products (not shown) according to the present invention. The article 10 comprises a housing 12 having a front wall 14, a back wall 16, a bottom 18, and opposite side walls 20, 22 which define an interior 24. Attached to the housing 12 is a cover 30 which extends from the back wall 16 and selectively covers or uncovers the interior 24 of the housing 12.

The cover 30 is held in a covering position over interior 24 by releasable securing means 32 such as hook and loop fasteners, zippers, snaps and the like.

In one embodiment, the interior surface 34 of the cover 30 contains a pocket 36 which can hold a panty shield, thin maxi pad or a pair of disposable panties. The pocket may be equipped with releasable securing means for securing items held therein. Because the pocket 36 holds items in a predetermined position within the housing interior 24 when the cover 30 is closed, protection is provided against the ripping of paper or plastic wrappings of the items held therein.

The housing 12 has a length L comparable to a tampon which is prepackaged with an associated applicator.

Hereinafter, "tampon" refers to both the actual tampon and its associated applicator. The housing 12 has a minimal width W able to accommodate two such tampons disposed in side by side relationship.

The article 10 of the present invention comprises a support member 40 for holding the tampons in a predetermined position within the housing 10. The support member 40 also reduces the likelihood of the tampons becoming crushed during transport.

The structures of the housing 12 and support member 40 are detailed more fully in FIGS. 2-5. In a preferred embodiment, the housing 12 comprises an exterior layer 42 made of a first material which gives a decorative look to the article 10. For instance, the exterior layer 42 may be made of silk, beaded fabric, leather and the like.

One essential feature of the present invention is interior layer, or lining, 44 of the housing 12. The lining 44 is made of a second, moisture-resistant material. Preferred lining materials include nylon, pre-treated fabric, plastic, etc. The lining 44 is generally disposed to the interior side of the exterior layer 42.

In addition, the housing 12 may include a reinforcing layer 46 disposed between the exterior layer 42 and the lining 44. The reinforcing layer 46 may be formed of coated cardboard or thin sheets of plastic. The reinforcing layer 46 acts to stiffen the housing 12.

Figure 3:
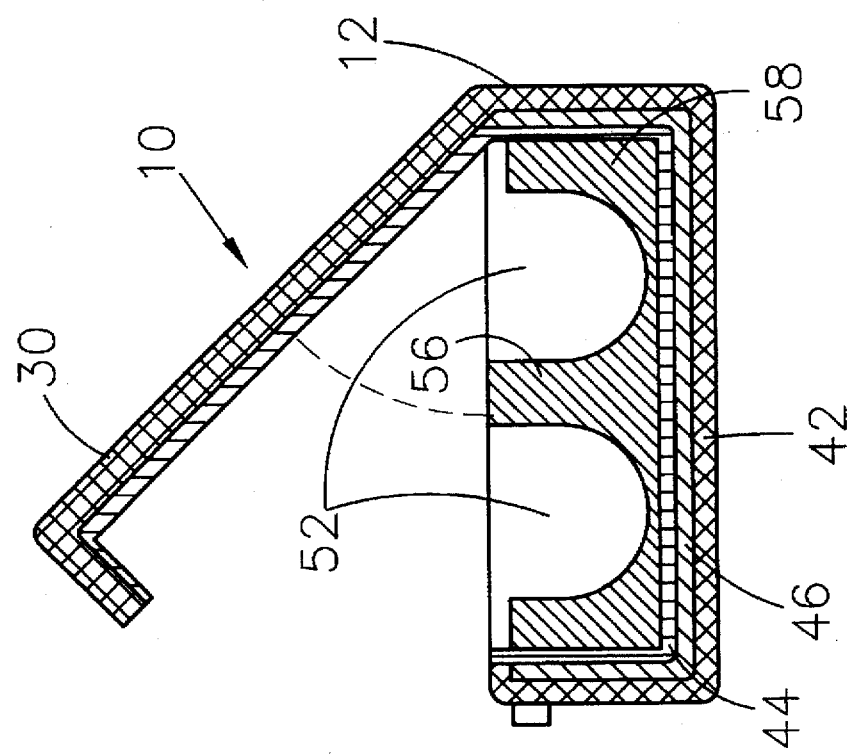
FIG. 3 is a transverse sectional view of a further embodiment of the invention.
Figure 2:
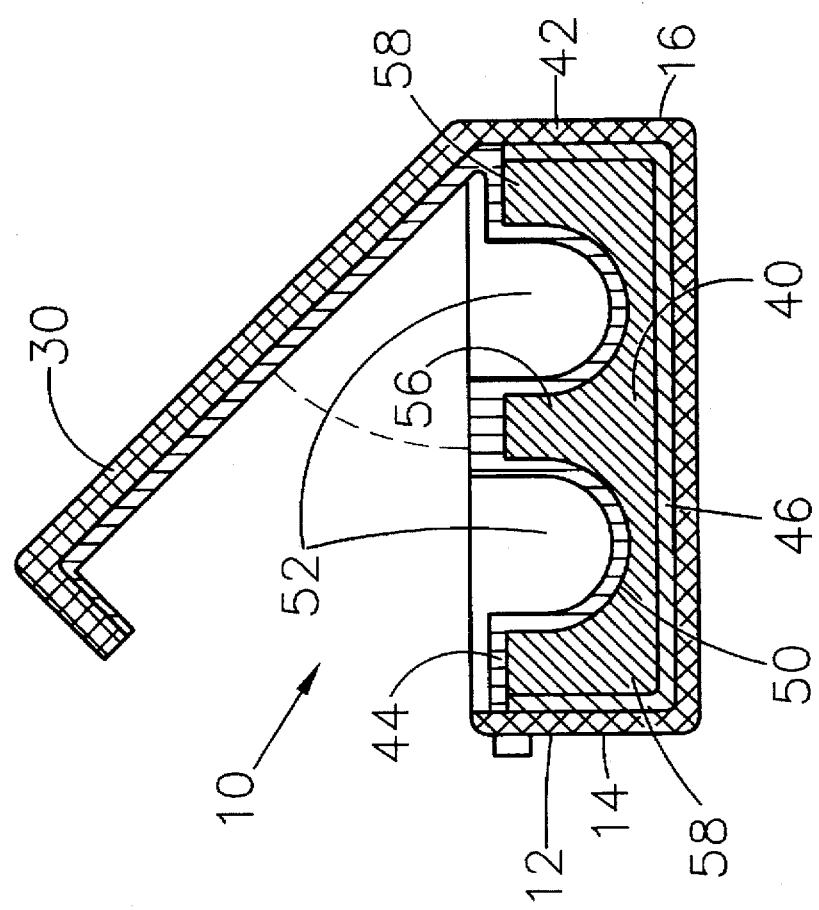
FIG. 2 is a transverse sectional view of one embodiment of the invention.

Another essential feature of the present invention is the inclusion of the protective support member 40 to resist crushing of tampons held within the article 10. The support member 40 may be formed of rigid or semi-rigid material such as molded plastic, cardboard and the like. As shown in FIG. 2, in one embodiment, the support member 40 is disposed between the exterior layer 42 and the lining 44. In another embodiment of the invention, as shown in FIG. 3, the support member 40 is disposed to the interior side of the lining 44.

The support member 40 includes an upper surface 50 which defines at least two parallel concave channels 52 which are adapted to receive cylindrical tampons therein. A partition 56 is positioned between the channels 52 to insure that the tampons are held in fixed relationship.

In a preferred embodiment, the support member 40 is disposed to the interior side of the lining 44 layer of the housing. In such an embodiment, it is further preferable to provide a support member 40 having decorative properties. For instance, a molded plastic support may be covered with decorative fabric to match the exterior layer 40.

The support member 40 may comprise any one of several cross-sectional profiles. As shown in FIGS. 2-3, the partition 56 may extend upwardly from the upper surface 50 of the support member 40 to engage a portion of the closed cover 30 to further secure the tampons and protect them from being crushed while being carried in the article 10. Likewise, the support member 40 may include walls 58 which are coextensive with the front and back walls 14, 16 of the housing 12.

The partition 56 may be molded to include opposite flanges 60 as shown in FIG. 4 to provide recessed grooves 62 to further engage tampons held therein.

With reference again to FIGS. 2-3, the cover 30 may be formed as an extension of the materials used for the exterior layer 42 and the moisture-resistant lining 44.

Figure 6:
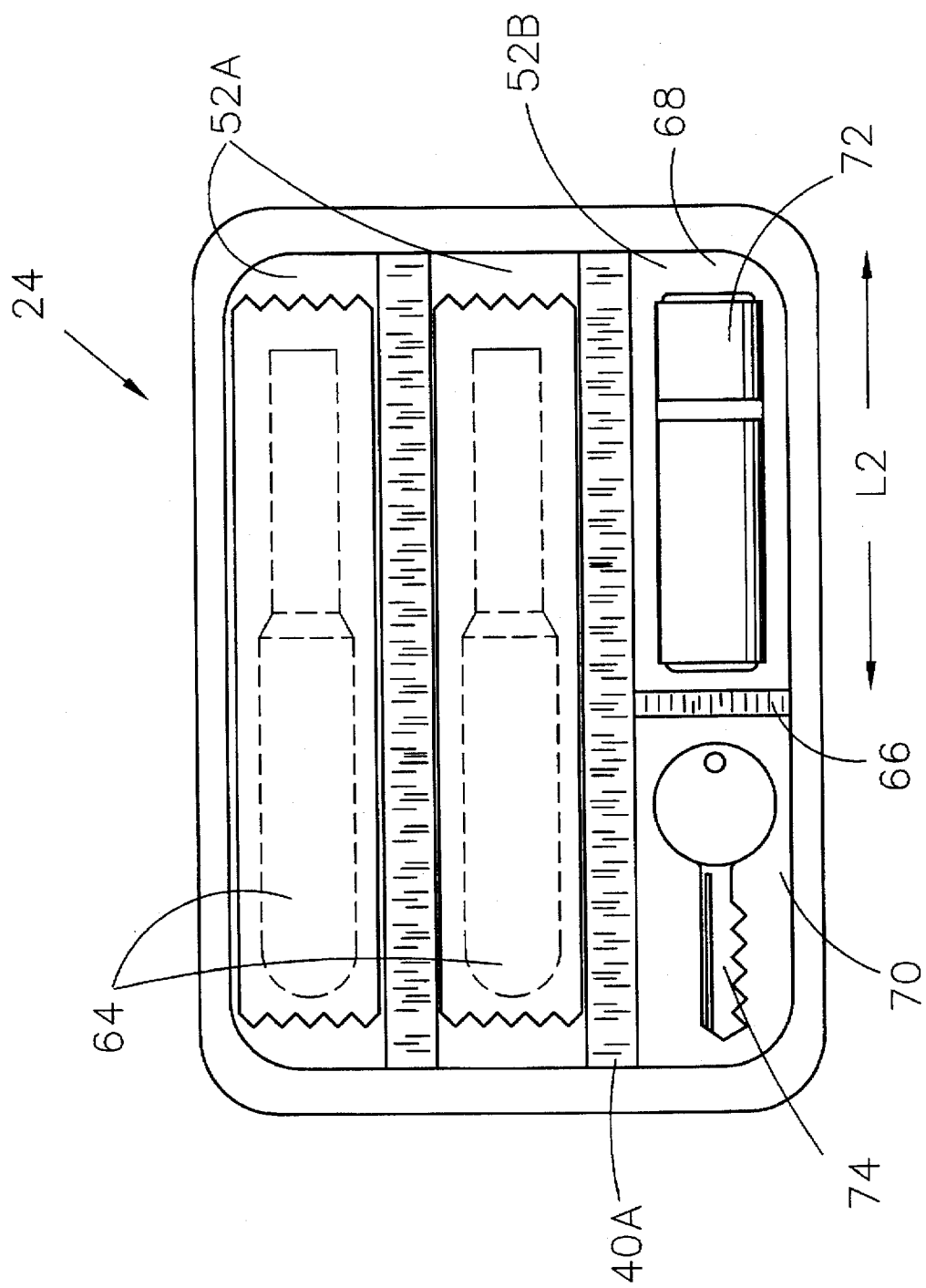
FIG. 6 is a top view of an interior of the housing according to one embodiment of the invention, including items that may be carried therein.

The interior 24 of a further embodiment of the invention is shown in FIG. 6. The housing 12 shown therein has a support member 40A having an upper surface 50A with three concave channels 52A, 52B therein. Two of the channels 52A can be used as in previous embodiments to hold tampons 64 during transport. The third channel 52B can carry an additional tampon, or other cylindrical items. One embodiment of the invention also includes a widthwise partition 66 in the third channel 52B which defines two separate compartments 68, 70. The first compartment 68 may have a length L2 comparable to a lipstick tube 72. The second compartment 70 may hold additional items such as coins and keys 74. In one embodiment of the invention, the second compartment 70 includes transverse grooves in the channel 52B for the reception of coins.

As shown in FIG. 7, the article 10 may include exterior pockets 76, 78 adapted to receive frequently carried items such as a driver's license, credit cards, change, or a house key in a manner similar to a wallet. The support member 40 protects the items carried in the interior 24 from damage by articles carried in the exterior pockets 74.

The preferred embodiments have been described hereinabove. It will be apparent to those skilled in the art that the above embodiments may incorporate changes and modifications without departing from the general scope of this invention. It is intended to include all such modifications and alterations in so far as they come within the scope of the appended claims or the equivalents thereof.

Having thus described the invention, it is now claimed:

1. An article for holding feminine hygiene products comprising:

a housing including a bottom, a front wall, a rear wall, and opposite side walls, and an open top disposed in communication with an interior of said housing, said housing comprising a first exterior layer and a second interior layer, said exterior layer being made of a first material and said interior layer being made of a second, moisture-resistant material;

a cover attached along one edge thereof to said back wall and disposed for placement in a covering relationship to said interior of said housing;

a support member disposed within said housing, said support member having a first surface having a plurality of parallel concave channels therein, adjacent channels being separated by an upwardly extending partition disposed therebetween; and, means for releasably securing said cover in said covering relationship.

2. The article of claim 1 wherein said housing further comprises stiffening means for stiffening said housing, said stiffening means being disposed between said exterior layer and said interior layer.

3. The article of claim 2 wherein said stiffening means comprises cardboard sheets.

4. The article of claim 1 wherein said support member engages a portion of said cover when said cover is placed in said covering relationship.

5. The article of claim 1 wherein said partition includes oppositely extending flanges.

6. The article of claim 1 wherein said support member comprises molded plastic material.

7. The article of claim 1 wherein said cover comprises an interior surface having a pocket therein.

8. The article of claim 1 wherein said cover comprises an exterior surface having a pocket therein.

9. The article of claim 1 wherein one of said channels comprises a transverse partition defining first and second chambers.

10. The article of claim 1 wherein said support member is disposed between said exterior layer and said interior layer.

11. The article of claim 1 wherein said support member includes first and second opposing walls, said first wall being co-extensive with said front wall and said second wall being co-extensive with said rear wall.

12. The article of claim 1 wherein said first material comprises leather.

13. The article of claim 1 wherein said first material comprises a textile fabric.

14. The article of claim 1 wherein said second material comprises nylon.

15. An article for holding feminine hygiene products comprising:

a housing including a bottom, a front wall, a rear wall, and opposite side walls, and an open top disposed in communication with an interior of said housing, said housing comprising a first exterior layer and a second interior layer, and a reinforcing layer disposed therebetween, said exterior layer being made of a first material and said interior layer being made of a second, moisture-resistant material;

a cover attached along one edge thereof to said back wall and disposed for placement in a covering relationship to said interior of said housing, said cover having a first pocket in an interior surface and a second pocket in an exterior surface;

a support member disposed within said housing, said support member having a first surface having parallel concave channels therein and an upwardly extending partition disposed between said channels; and, means for releasably securing said cover in said covering relationship.

16. The article of claim 15 wherein said support member engages a portion of said cover when said cover is in said covering relationship.

17. The article of claim 15 wherein said support member further comprises a first wall co-extensive with said front wall and a second wall co-extensive with said rear wall.

* * * * *